US008802165B2

(12) United States Patent
Bartolomé Sualdea et al.

(10) Patent No.: US 8,802,165 B2
(45) Date of Patent: Aug. 12, 2014

(54) PHENOLIC EXTRACTS OF ALMOND PEEL CONTAINING PROCYANIDINS, PROPELARGONIDINS, AND PRODELPHINIDINS, AND METHOD FOR PREPARATION THEREOF

(75) Inventors: Begoña Bartolomé Sualdea, Madrid (ES); María Monagas Juan, Madrid (ES); Ignacio Garrido Lafuente, Madrid (ES); María Carmen Gómez-Cordovés De La Vega, Madrid (ES); Rosa Lebrón Aguilar, Madrid (ES); José Carlos Quintela Fernandez, Madrid (ES); Esther De La Fuente García, Madrid (ES); Alejandro Jara García-Navas, Madrid (ES)

(73) Assignees: Consejo Superior de Investigaciones Cientificas, Madrid (ES); Biosearch, S.A., Granada (ES)

( * ) Notice: Subject to any disclaimer, the term of this patent is extended or adjusted under 35 U.S.C. 154(b) by 467 days.

(21) Appl. No.: 12/664,350

(22) PCT Filed: May 28, 2008

(86) PCT No.: PCT/ES2008/070104
§ 371 (c)(1),
(2), (4) Date: Mar. 1, 2010

(87) PCT Pub. No.: WO2008/152173
PCT Pub. Date: Dec. 18, 2008

(65) Prior Publication Data
US 2010/0184850 A1    Jul. 22, 2010

(30) Foreign Application Priority Data
Jun. 12, 2007  (ES) .................................. 200701616

(51) Int. Cl.
*A61K 36/736* (2006.01)
(52) U.S. Cl.
USPC .......................................... 424/735; 514/456
(58) Field of Classification Search
None
See application file for complete search history.

(56) References Cited

U.S. PATENT DOCUMENTS

| 2002/0028260 A1 | 3/2002 | Walker et al. | |
| 2003/0060426 A1* | 3/2003 | Pflucker et al. | 514/27 |
| 2004/0028758 A1* | 2/2004 | Park et al. | 424/765 |
| 2004/0156925 A1 | 8/2004 | Howell et al. | |

FOREIGN PATENT DOCUMENTS

| ES | 2 171 142 | 8/2002 |
| WO | WO99/12541 | 3/1999 |
| WO | WO2004/112813 | 12/2004 |
| WO | WO2005/072726 | 8/2005 |

OTHER PUBLICATIONS

Monagas (J. Agric. Food Chem. (Sep. 2007), vol. 55, pp. 8498-8507).*
Garrido I., et al., Hydrophilic and lipophilic antioxidant capacities of commercial dietary antioxidant supplements. Ital. J. Food Sci., n. 3, vol. 19, 343-350, 2007.
Porter L.J. Flavans and proanthocyanidins, The Flavonoids, Edited by J.B. Harborne, Chapman and Hall Ltd, 1988.
Prior R.L., et al., Occurrence and biological significance of proanthocyanidin in the American diet. Phytochemistry 66, 2264-2280, 2005.
Foo L.Y., et al. A-type proanthocyanidin trimers from cranberry that inhibit adherence of uropathogenic P-fimbriated *Escherichia coli.*, 2000, J Nat. Prod. 63, 1225-1228.
Foo L.Y., et al. The structure of cranberry proanthocyanidins which inhibit adherence of uropathogenic P-fimbriated *Escherichia coli* in vitro., 2000, Phytochemistry 54, 173-181.
Anderson R.A., et al., Isolation and characterization of polyphenol A-type polymers from cinnamon with insulin-like biological activity., 2004, J. Agric. Food Chem. 52, 65-70.
Lin L.C., et al. Immunomodulatory proanthocyanidins from *Ecdysanthera utilis.*, 2002, J. Nat. Prod. 65, 505-508.
Sang, S.; et al. Antioxidant phenolic compounds isolated from almond skins (*Prunus amygdalus* Batsch)., 2002, J. Agric. Food Chem., 50, 2459-2463.
Milbury P.E., et al. Determination of flavonoids and phenolics and their distribution in almonds., 2006, J Agric Food Chem 54, 5027-5033.
Wijeratne SSK, et al. Antioxidants polyphenols in almond and its coproducts., 2006, J Agric Food Chem, 54, 312-318.
Brieskom, C.H.; et al. Procyanidin polymers crucial to the structure of the almond seed coat., 1998, Z. Lebensm. Unters. Forsch. 187, 347-353.
Lazarus S.A., et al. High performance liquid chromatography/mass spectrometry analysis of proanthocyanidins in food and beverages., 1999, J. Agric. Food Chem. 47, 3693-3701.
Singleton V.L., et al. Colorimetry of total phenolics with phosphomolibdicphosphotungstic acid reagent., 1965, Am J Enol Vitic 16, 144-158.

(Continued)

*Primary Examiner* — Susan Hoffman
(74) *Attorney, Agent, or Firm* — K&L Gates LLP

(57) ABSTRACT

The present disclosure concerns phenolic extracts containing procyanidins, propelargonidins and prodelfinidins obtained from peel of the almond [*Prunus dulcís* (Mili.) D. A. Webb, *Prunus amygdalus* (L.) Batsch., *Amygdalus dulcís* (Mili.), *Amygdalus communis* (L.) or *Prunus communis* (L.)]. In particular, the objective is to obtain extracts rich in proanthocyanidins with type-A bonds. The preparation method disclosed comprises: (a) a maceration of plant material with organic solvents at 25-100° C., (b) purification by liquid-liquid extraction and/or adsorption or ion exchange chromatography, and (c) optionally, a final drying. Also disclosed are the possible activities/properties of these extracts such as antioxidant activity and others, which determine the use thereof as a nutritional or health ingredient, and the use thereof in the cosmetic and pharmaceutical industry.

24 Claims, 7 Drawing Sheets

(56) References Cited

OTHER PUBLICATIONS

Reed J.D., et al. MALDI-TOF mass spectrometry of oligomeric food polyphenols., 2005, Phytochemistry 66, 2248-2263.

Prior R.L., et al. Standardized methods for the determination of antioxidant capacity of phenolics in foods and dietary supplements., 2005 J. Agric. Food Chem. 53, 4290-4302.

Monagas M., et al. Quality assessment of commercial dietary antioxidant products from *Vitis vinifera* I. grape seeds., 2005, Nutr. Cancer, 53, 244-254.

Monagas M., et al. Commercial dietary ingredients from *Vitis vinifera* L. leaves and grape skins: antioxidant and chemical characterization., 2006, J. Agric. Food Chem., 54, 319-327.

Barreiros A. L.B.S., et al., A-type proanthocyanidin antioxidant from Dioclea lasiophylla, 2000, Phytochemistry, 55, 805-808.

Gu et al. "Screening of Foods Containing Proanthocyanidins and Their Structural Characterization Using LC-MS/MS and Thiolytic Degradation", Journal of Agricultural and Food Chemistry, 2003, vol. 51, pp. 7513-7521.

Cifuentes et al. "Fast determination of procyanidins and other phenolic compounds in food samples by micellar electrokinetic chromatography using acidic buffers", Electrophoresis, May 2001, vol. 22, No. 8, pp. 1561-1567.

Harnly et al. "Flavonoid Content of U.S. Fruits, Vegetables, and Nuts", Journal of Agricultural and Food Chemistry, 2006, vol. 54, No. 26, pp. 9966-9977.

\* cited by examiner

PHENOLIC EXTRACTS OF ALMOND PEEL CONTAINING PROCYANIDINS, PROPELARGONIDINS, AND PRODELPHINIDINS, AND METHOD FOR PREPARATION THEREOF

CROSS REFERENCE TO RELATED APPLICATIONS AND PRIORITY CLAIM

This application claims the benefit under 35 U.S.C. §371 to PCT/EP2008/070104 filed May 28, 2008, which claims the benefit of Spanish Patent Application No. P200701616 filed Jun. 12, 2007. The entire disclosures of both applications are incorporated herein by reference thereto.

BACKGROUND

1. Technical Field

Bioactive phenolic extracts applicable in the food, dietary, cosmetic and pharmaceutical industry.

2. Relevant-Background

Proanthocyanidinins or condensed tannins are oligomers and polymers of flavan-3-ol widely distributed in the plant kingdom. The most abundant units of flavan-3-ol are (+)-afzelechin, (+)-catechin and (+)-gallocatechin (forms 2R:3S) and their diastereoisomer (−)-epiafzelechin, (−)-epicatechin and (−)-epigallocatechin (forms 2R:3R), respectively. Proanthocyanidinins exclusively constituted by (epi)catechin are called procyanidins. Propelargonidins and prodelphinidins contain at least one unit of (epi)afzelechin and (epi)gallocatechin, respectively, together with units of (epi)catechin. In the B-type procyanidins/propelargonidins/prodelphinidins, the units of flavan-3-ol are bound by the C-4 carbon of the upper unit and the C-6 or C-8 carbon of the lower unit, C4-C8 isomers being more abundant than C4-C6. In addition to this interflavonic C—C bond, the A-type procyanidins have a bond of ether-type between the C-2 carbon of the upper unit and the hydroxyl group of the C-7 of the lower unit (Porter L. J. (1988) Flavans and proanthocyanidins. In *The flavonoids* (Harborne J. B., Ed.) Chapman and Hall, New York, pp. 21-62). Whilst B-type proanthocyanidinins are found in many plant species, there a few natural sources where A-type proanthocyanidinins have been identified (bilberry, peanut, avocado, plum, cinnamon and curry); likewise, procyanidins are the majority with respect to propelargonidins and prodelphinidins in the plant kingdom (Prior R. L., Gu L. (2005) Occurrence and biological significance of proanthocyanidin in the American diet. *Phytochemistry* 66, 2264-2280).

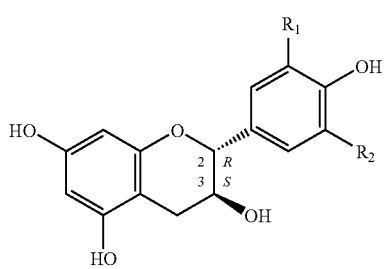

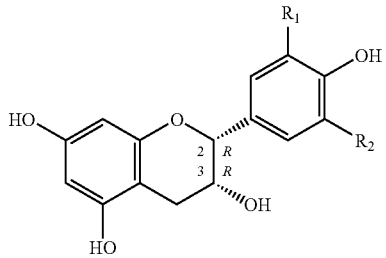

| Flavan-3-ol | $R_1$ | $R_2$ | C-2 | C-3 |
|---|---|---|---|---|
| (+)-Afzelechin | H | H | R | S |
| (+)-Catechin | H | OH | R | S |
| (+)-Gallocatechin | OH | OH | R | S |
| (−)-Epiafzelechin | H | H | R | R |
| (−)-Epicatechin | H | OH | R | R |
| (−)-Epigallocatechin | OH | OH | R | R |

Products rich in proanthocyanidinins most widely marketed at present are currently obtained from sources such grape seeds, apple, cocoa, pine bark, etc., and mainly contain B-type procyanidins. A-type proanthocyanidinins have properties/activities that are potentially beneficial for human health, such as reduction of the capacity of bacterial adhesion in the urinary tract—which reduces the risk of urinary infections (Foo L. Y., Lu Y. R., Howell A. B., Vorsa N. (2000) A-type proanthocyanidin trimers from cranberry that inhibit adherence of uropathogenic P-fimbriated *Escherichia coli*. *J Nat. Prod.* 63, 1225-1228; Foo L. Y., Lu Y. R., Howell A. B., Vorsa N. (2000) The structure of cranberry proanthocyanidins which inhibit adherence of uropathogenic P-fimbriated *Escherichia coli* in vitro. *Phytochemistry* 54, 173-181), and the pseudoinsulin activity, which improves glucose metabolism in patients with type 2 diabetes—(Anderson R. A., Broadhurst C. L., Polansky M. M., Schmidt W. F., Khan A., Flanagan V. P., Shoene N. W., Graves D. J. (2004) Isolation and characterization of polyphenol A-type polymers from cinnamon with insulin-like biological activity. *J. Agric. Food Chem.* 52, 65-70). Antioxidant activities have also been demonstrated (Barreiros A. L. B. S., David J. P., de Queiroz L. P., David J. M. (2000) A-type proanthocyanidin antioxidant from *Dioclea lasiophylla*. *Phytochemistry* 55, 805-808) as have anti-inflammatory activity (Lin L. C., Kuo Y. C., Chou C. J. (2002) Immunomodulatory proanthocyanidins from *Ecdysanthera utilis*. *J. Nat. Prod.* 65, 505-508) for A-type proanthocyanidinins.

Having stated the above, the interest therefore arises for new products rich in the three types of proanthocyanidinins—i.e., procyanidins, propelargonidins, and prodelphinidins—especially with A-type bonds. Some earlier publications related to products containing proanthocyanidinins are the following:

WO2005/072726: Compositions and methods of use of A-type procyanidins, Schmitz, H. H.; Kwik-Uribe, C. L.; Kelm, M. A.; Hammerstone, J. F. This publication relates to formulations to be used in treatment for hypertension. A-type procyanidins are exclusively included, in other words, formed exclusively by (epi)catechin.

WO2004/112813: Litchi sinensis extracts containing oligomeric proanthocyanidins, Rull, S.; Alaoui, I.; Fabry, B. This publication relates to the preparation of litchi extracts rich in A-type proanthocyanidinins, although identifications of the type of molecules contained in the extract are not included.

US2004/156925: Plant proanthocyanidin extract effective at inhibiting utility, Howell, A. B.; Vorsa, N. This publication relates to the preparation of extracts of proanthocyanidinins for the prevention and treatment of infections of the urinary tract caused by *Escherichia coli* type P. The extracts contain proanthocyanidinins with at least one A-type bond, particularly procyanidins.

WO99/12541: Plant proanthocyanidin extract effective at inhibiting adherence of bacteria with P-type fimbriae to surfaces, Howell, A. B.; Vorsa, N. This publication relates to the preparation of extracts of proanthocyanidinins from the Ericaceae, Rosaceae, Pinaceae and Vitaceae families, preferably *Vaccinium macrocarpon*. The extracts are used in the prevention and treatment of urinary tract infections caused by P-type *Escherichia coli*.

US2002/028260: Proanthocyanidin composition extracted from Vaccinium useful in pharmaceutical compositions for preventing or treating urogenital infection, Mickelsen, J. N.; Mickelsen, R. A.; Walker, E. B. This publication relates to the use of certain procyanidins (A and B) against urinary infections and others. Although the title speaks of proanthocyanidinins, in the text it indicates that they are formed by (epi) catechin units, (i.e. procyanidins).

US2002/0228260: Plant proanthocyanidin extracts, Walter, E. B.; Mickelsen, R. A.; Mickelsen, J. N. This publication relates to plant extracts containing procyanidins with at least one A-type bond and their use in the prevention and treatment of urogenital infections.

ES2171142: Flavanol and cysteamine conjugates. Torres, J. L. It relates to new products which result from the conjugation of polyphenolic extracts rich in procyanidins and prodelphinidins with molecules which contain the thiol group.

An important point in development of products rich in potentially active compounds is their cost, both of initial raw material and preparation method. In this sense, food industry by-products are attractive sources of bioactive compounds.

The tegument or skin of the almond, which is separated from the almond during the industrial processing thereof, is a by-product with little economic value, mainly used as cattle fodder. Various phenolic compounds have been identified in almond skin, both of non-flavanoid type and flavanoid type (Sang, S.; Lapsley, K.; Jeong, W-S.; Lachance, P. A.; Ho, C-T; Rosen, R. T. (2002) Antioxidant phenolic compounds isolated from almond skins (Prunus amygdalus Batsch). *J. Agric. Food Chem.,* 50, 2459-2463; Milbury P. E., Chen C. A N D., Dolnikowski G. G., Blumberg J. B. (2006) Determination of flavonoids and phenolics and their distribution in almonds. *J Agric Food Chem* 54, 5027-5033; Wijeratne S S K, Abou-Zaid M M, Shahidi F. (2006) Antioxidants polyphenols in almond and its coproducts. *J Agric Food Chem,* 54, 312-318). In relation to flavan-3-ols, Brieskon, C. H.; Betz, R. (1998) Procyanidin polymers crucial to the structure of the almond seed coat. *Z. Lebensm. Unters. Forsch.* 187, 347-353, identified the monomers (+)-catechin and (−)-epicatechin, as well as the dimmers of procyanidins B1, B3 and B4. Later, Lazarus, S. A., Adamson, G. E., Hammerstone, J. F., Schmitz, H. H. (1999) High performance liquid chromatography/mass spectrometry analysis of proanthocyanidins in food and beverages. *J. Agric. Food Chem.* 47, 3693-3701, confirms the presence of B-type procyanidins, also demonstrating the absence of A-type procyanidins in the extracts obtained from almond skin.

DETAILED DESCRIPTION OF THE PREFERRED EMBODIMENTS

Figure 1:
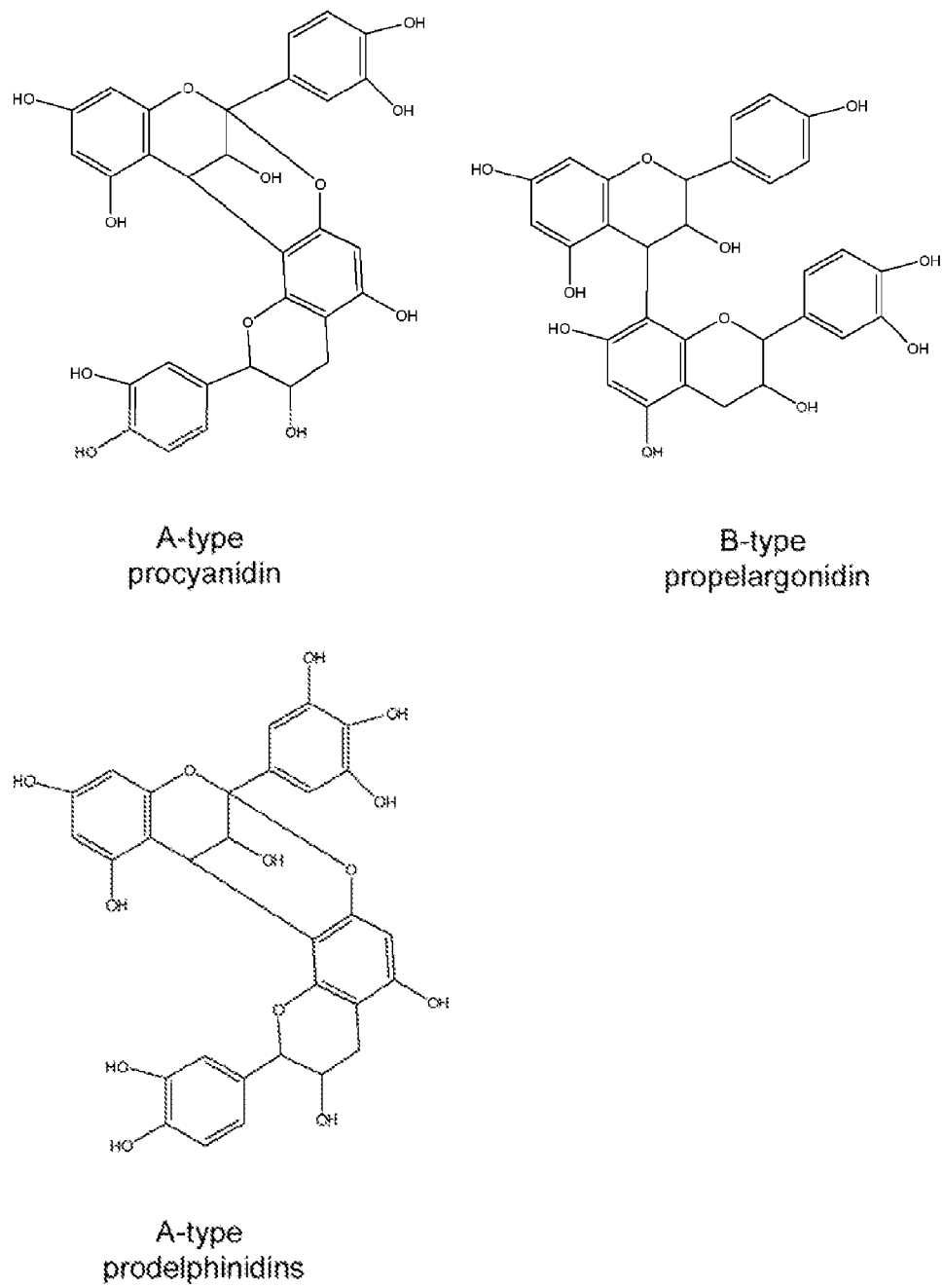
FIG. 1 illustrates examples of the chemical structures of the proanthocyanidinins which would be found in the extracts disclosed herein.

The preparation of extracts containing proanthocyanidinins with properties/activities that are potentially beneficial for human health are disclosed herein. Furthermore, low cost raw materials and simple and profitable production processes are described.

The present disclosure relates to phenolic extracts containing procyanidins, propelargonidins, and prodelphinidins, and prepared from almond skin [*Prunus dulcis* (Mill.) D. A. Webb, *Prunus amygdalus* (L.) Batsch., *Amygdalus dulcis* (Mill.), *Amygdalus communis* (L.) or *Prunus communis* (L.)]. In particular, it is desired to achieve proanthocyanidin-rich extracts with A-type bonds. It is expected that these extracts have different properties, if not improved, with respect to the products currently commercially marketed and which mainly contain B-type procyanidins.

The preparation method disclosed herein consists of a maceration of plant material with solvents, followed by a purification stage of the extract and, optionally, a final drying of the purified extract. Possible activities or properties of these extracts are disclosed, such as antioxidant activity and others, which determine their use as food or dietary ingredient and in the cosmetics and pharmaceutical industry.

The present disclosure relates to phenolic extracts of almond skin (tegument) [*Prunus dulcis* (Mill.) D. A. Webb, *Prunus amygdalus* (L.) Batsch., *Amygdalus dulcis* (Mill.), *Amygdalus communis* (L.) or *Prunus communis* (L.)] characterized in that they contain procyanidins, propelargonidins, and prodelphinidins. Almond skin is a low-cost food by-product, which means that this extract preparation method would involve the reuse of said by-product since products of greater added value would be obtained. The skin could be used both wet and dry, separated from the fruit by a blanching process and later peeling, or by toasting.

Procyanidins are polymers formed only by (+)-catechin and/or (−)-epicatechin. On the other hand, propelargonidins and prodelphinidins are polymers that contain units of (+)-afzelechin and/or (−)-epiafzelechin—case of propelargonidins- and of (+)-gallocatechin and/or (−)-galloepicatechin—case of prodelphinidins-, possibly also containing units of (+)-catechin and/or (−)-epicatechin. The structural differences between (epi)catechin (dihydroxy-substitution in the B-ring) and (epi)afzelechin (monohydroxy-substitution in the B-ring) and (epi)gallocatechin (trihydroxy-substitution in the B-ring) would justify possible peculiarities in the physiological properties/activities of these three groups of proanthocyanidinins. It should, therefore, be expected that extracts containing combinations of these three types of proanthocyanidinins would have different properties, if not improved, with respect to the products currently marketed and which only contain procyanidins.

Another structural characteristic of proanthocyanidinins that determines their physiological properties/activities is the type of bond (A or B) between the forming units. The present disclosure also relates to almond skin extracts characterized in that they contain A-type procyanidins, propelargonidins, and prodelphinidins.

The total phenolic content of the extract is determined by the colorimetric method of Singleton V. L., Rossi J. A. (1965) Colorimetry of total phenolics with phosphomolibdicphosphotungstic acid reagent. *Am J Enol Vitic* 16, 144-158, which is based on oxidation in base medium of the hydroxyl groups of phenols by Folin-Ciocalteu reagent. The results are expressed as gallic acid/g of extract. In this way, the extracts obtained following the processes which are detailed below have a total minimum phenolic content of 50 mg/g (5%).

To confirm that the extracts contain the three types of proanthocyanidinins (procyanidins, propelargonidins, and prodelphinidins) bound both by A or B-type bonds, a mass spectrometry analysis is performed, specifically MALDI-TOF-MS ("matrix-assisted laser desorption/ionization time-of-flight mass spectrometry"). For this analysis, the extract is crystallized in a solid matrix whereon the laser hits, which produces ionization of the molecules contained in the extract. The ions formed migrate due to the effect of an electric field and do so in accordance with their mass/charge ratio (m/z), which allows determining the molecular mass of the substances contained in the extract. The low ionization energy and the high transmission efficacy make this technique one of the most resolvent for the study of proanthocyanidinins (Reed J. D., Krueger C. G., Vestling M. M. (2005) MALDI-TOF mass spectrometry of oligomeric food polyphenols. *Phytochemistry* 66, 2248-2263).

The following table indicates the monoisotopic masses corresponding to the sodium adducts of B and A-type procyanidins, propelargonidins, and prodelphinidins which would be found in the extracts disclosure herein. The assignment of the structure to the mass observed $[M+Na]^+$ (m/z) is performed bearing in mind the theoretical calculation: $m/z=290.08*(CAT)+274.08*(AFZ)+306.07*(GAL)-2.02*(B)-4.04*(A)+22.99$, where CAT, AFZ and GAL correspond, respectively, to the number of units of (epi)catechin, (epi)afzelechin and (epi)gallocatechin which compose the proanthocyanidin molecule; B and A correspond, respectively, to the number of B and A-type bonds between the constitutive units. By way of example, the m/z signals are collected corresponding to procyanidins, propelargonidins [up to 2 units of (epi)afzelechin] and prodelphinidins [up to 2 units of (epi)gallocatechin] with B and A-type bonds.

MALDI-TOF-MS Signals $[M+Na]^+$ (m/z)

| | Procyanidins | | Propelargonidins 1 (epi)afzelechin unit | | Propelargonidins 2 (epi)afzelechin units | |
|---|---|---|---|---|---|---|
| g | B-type | A-type 1 bond | B-type | A-type 1 bond | B-type | A-type 1 bond |
| 2 | 601 | 599 | 585 | 583 | 569 | 567 |
| 3 | 889 | 887 | 873 | 871 | 857 | 855 |
| 4 | 1177 | 1175 | 1161 | 1159 | 1145 | 1143 |
| 5 | 1465 | 1463 | 1449 | 1447 | 1433 | 1431 |
| 6 | 1753 | 1751 | 1737 | 1735 | 1721 | 1719 |
| 7 | 2041 | 2039 | 2025 | 2023 | 2009 | 2007 |
| 8 | 2329 | 2327 | 2313 | 2311 | 2297 | 2295 |
| 9 | 2617 | 2615 | 2601 | 2599 | 2585 | 2583 |
| 10 | 2905 | 2903 | 2889 | 2887 | 2873 | 2871 |

MALDI-TOF-MS Signals $[M+Na]^+$ (m/z)

| | Prodelphinidins 1 (epi)gallocatechin unit | | Prodelphinidins 2 (epi)gallocatechin units | |
|---|---|---|---|---|
| g | Type B | A-type 1 bond | B-type | A-type 1 bond |
| 2 | 617 | 615 | 633 | 631 |
| 3 | 905 | 903 | 921 | 919 |
| 4 | 1193 | 1191 | 1209 | 1207 |
| 5 | 1481 | 1479 | 1497 | 1495 |
| 6 | 1769 | 1767 | 1785 | 1783 |
| 7 | 2057 | 2055 | 2073 | 2071 |
| 8 | 2345 | 2343 | 2361 | 2359 |
| 9 | 2633 | 2631 | 2649 | 2647 |
| 10 | 2921 | 2919 | 2937 | 2935 | g-Degree of polymerization.

In addition to the MALDI-TOF analysis, the extracts are analysed by high performance liquid chromatography coupled to mass spectrometry (HPLC/MS) to separate from one another the different isomers from the dimers and trimers of procyanidins, propelargonidins, and prodelphinidins, both with B-type and A-type bonds. Since there are barely commercial standards for proanthocyanidinins, the identification of the chromatographic peaks is based on its mass spectrometry, which allows us to know the forming units (although without distinguishing between diasteroisomers). The assignment of the structure to the mass observed $[M-H]^-$ (m/z) is made in accordance with the following expression: $m/z=290.08*(CAT)+274.08*(AFZ)+306.07*(GAL)-2.02*(B)-4.04*(A)-1.01$, where CAT, AFZ and GAL correspond, respectively, to the number of units of (epi)catechin, (epi)afzelechin and (epi)gallocatechin which compose the proanthocyanidin molecule; B and A correspond, respectively, to B and A-type bonds between the constitutive units. By way of example, next, the m/z signals are included corresponding to dimers and trimers of procyanidins, propelargonidins, and prodelphinidins with B and A-type bonds.

ESI-MS signals [M-H]⁻ (m/z)

|  | Procyanidins | | Propelargonidins 1 (epi)afzelechin unit | | Prodelphinidins 1 (epi)gallocatechin unit | |
| --- | --- | --- | --- | --- | --- | --- |
| g | B-type | A-type 1 bond | B-type | A-type 1 bond | B-type | A-type 1 bond |
| 2 | 577 | 575 | 561 | 559 | 593 | 591 |
| 3 | 865 | 863 | 849 | 847 | 881 | 879 | g-Degree of polymerization.

Some examples of the chemical structures of proanthocyanidinins that would be found in the extracts that are the subject of this disclosure are shown in FIG. 1.

To quantify the proanthocyanidinins identified, a fluorescence detector is used operating in specific conditions for flavan-3-ols ($\lambda_{excitation}$=280 nm, $\lambda_{emission}$=310 nm). The contents of each compound are expressed in mg of (−)-epicatechin/g of extract. In this way, the extracts obtained have a minimum content of monomers, dimers and trimers of proanthocyanidinins of 10 mg/g (1%).

The percentage of A-type proanthocyanidinins is calculated by dividing the contents of A-type dimers and trimers by the content of the A and B-type dimers and trimers. In this way, the extracts obtained have a minimum percentage of A-type proanthocyanidinins of 15%.

Another aspect of the disclosure is a preparation method for the extracts in which some of the following steps are carried out:
- maceration of plant material with solvents;
- purification of the extract;
- drying of the purified extract.

The process starts with the wet or dry almond skin obtained after blanching and later peeling, or after toasting the almond. If the sample is dry, it can be ground to reduce the size. To avoid possible interferences of the fat, the skin can be defatted using organic solvents (e.g. hexane).

The extraction can be carried out with pure methanol, ethanol, and water, or mixtures thereof; at a temperature between 25° C. and 100° C., and preferably between 50° C. a 70° C.; acidulated or not with any acid of inorganic type such as, for example, HCl, $H_2SO_4$, or $H_3PO_4$, or any organic acid such as acetic acid or citric acid, or any cationic resin in protonated form. Typical systems are used for the solid-liquid extractions (incubator, reflux, etc.), it also being possible to use an ultrasound bath. The extraction time can be, according to the type of equipment used, between 2 hours and 24 hours. After this time, the liquid extract is separated from the solid residue by centrifugation or by pressing and/or filtration.

An alternative that accelerates the previous process and reduces the extracting liquid volume is extraction with overheated liquids. The extraction vehicle can also be pure methanol, ethanol, and water, or mixtures thereof, and acidulated or not with the same aforementioned acids. In this case, a specific extractor apparatus is used which allows using liquids at high temperatures and pressures between 500 psi and 3000 psi and temperatures between 60° C. and 180° C., preferably 100° C. to 140° C. The extraction time with overheated liquids may be, according to the conditions used, between 1 minute and 6 hours.

As regards the purification stage of the extract, one of the methods contemplated is extraction with organic solvents such as ethyl acetate, acetone, n-butanol, iso-propanol, or mixtures thereof, and acidulated with the same acids used in the extraction process.

Another alternative is purification by adsorption or ion exchange chromatography on Dowex or Amberlite type resins in gradient of methanol or ethanol-type alcohols between 20% and 80% alcohol.

The extract can be dried in different ways, although it is characterized by working at temperatures lower than 40° C. Lyophilisation, concentration and/or vacuum drying, air drying, and spraying are also included in the forms of drying.

As regards its properties, the extracts of almond skin described herein have antioxidant capacity, evaluated in vitro by the ORAC method (oxygen radical absorption capacity) using fluorescein as fluorescent substance. The antioxidants present in the extract neutralize the peroxyl radicals generated by the thermal decomposition of AAPH, thus avoiding its reaction with fluorescein. The results are expressed as mmols of Trolox/g of extract, Trolox being a synthetic compound, water-soluble analogue of vitamin E. The ORAC method is one of those recommended for measuring the antioxidant properties of foods and dietary products, as well as quality control thereof (Prior R. L., Wu X., Schaich K. (2005) Standardized methods for the determination of antioxidant capacity of phenolics in foods and dietary supplements. *J. Agric. Food Chem.* 53, 4290-4302).

At present, it is known that oxidative stress or oxidative overload is involved in a multitude of degenerative diseases, such as cancer, atherosclerosis, Alzheimer's disease or the aging process itself. But the etiopathogenic mechanisms are not completely known. Against oxidative stress as a cause of these diseases, a preventive strategy is considered to be a diet rich in antioxidant compounds, among them, phenolic compounds. But the fact that an extract has good in vitro properties does not necessarily entail that it acts as an effective in vivo antioxidant. Other factors such as bioavailability, metabolism, interactions among nutrients, etc. may condition the activity of the physiological medium of the potentially bioactive compound(s) present in the extract.

In any case, the ORAC methodology is a good experimental approximation for optimizing preparation processes, quality control and comparison between potentially active extracts. By way of reference, we can mention the ORAC values for some commercial phenolic extracts. The differences in antioxidant capacity among products are not only due to the source used, which determines the active phenolic structures, but also the extract preparation process.

| Source | Antioxidant activity ORAC (mmol Trolox/g) | Reference |
| --- | --- | --- |
| Grape seed (*Vitis Vinifera* L.) (n = 16) | 2.71-26.4 | Monagas et al., 2005 |
| Grape skin (*Vitis Vinifera* L.) (n = 11) | 2.23-6.32 | Monagas et al., 2006 |
| Piquette (*Vitis Vinifera* L.) (n = 2) | 13.3-21.4 | Monagas et al., 2006 |
| Vine leaves (*Vitis Vinifera* L.) (n = 4) | 1.52-2.55 | Monagas et al., 2006 |
| Pine bark *Pinus halepensis* L.) (Pycnogenol ®) | 3.15 | Garrido et al., 2007 |

-continued

| Source | Antioxidant activity ORAC (mmol Trolox/g) | Reference |
|---|---|---|
| Olive leaves (*Olea europea* L.) (Olixxol ®) | 4.20 | (unpublished data) |

References

Monagas M., Hernández-Ledesma B., Garrido I., Martin-Alvarez P. J., Gómez-Cordoves C., Bartolomé, B. (2005). Quality assessment of commercial dietary antioxidant products from *Vitis Vinifera* l. grape seeds. Nutr. Cancer, 53, 244-254.
Monagas M., Hernández-Ledesma B., Gómez-Cordovés C., Bartolomé, B. (2006). Commercial dietary ingredients from *Vitis vinifera* L. leaves and grape skins: antioxidant and chemical characterization. J. Agric. Food Chem., 54, 319-327.
Garrido I., Bartolomé B., Gómez-Cordovés C. (2007). Hydrophilic and lipophilic antioxidant capacities of commercial dietary antioxidant supplements. Ital. J. Food Sci., in press.

The extracts described herein have an antioxidant capacity similar or superior to those found for many of the phenolic extracts marketed at present. In any case, these extracts can also have other activities/properties of interest for the food, dietary, cosmetic and pharmaceutical industries. Thus, for example, it is expected that extracts containing A-type procyanidins, propelargonidins, and prodelphinidins have activities described for isolated molecules such as the inhibitory capacity of bacterial adhesion in the urinary tract and certain pseudoinsulin activity.

These extracts could be used as ingredients in foods, for the preparation of dietary supplements and cosmetics, and in drug manufacturing.

Throughout the description and the claims, the word "comprise" and its variants is not intended to exclude other technical characteristics, additives, components or steps. For those skilled in the field, other objects, advantages and characteristics of the invention will become apparent from the disclosure.

The invention will now be described in more detail by way of examples. The following examples are for illustrative purposes only and are not intended, nor should they be interpreted, to limit the scope of the appended claims.

EXAMPLES

Example 1

Extract of Almond Skin Containing Procyanidins, Propelargonidins, and Prodelphinidins Samples of almond skin are used that are shed during toasting the fruit in an industrial scale oven. The skins are ground. The ground sample was defatted with hexane. The defatted sample was mixed with methanol/HCl (1000:1 v/v) and was maintained for 15 min in an ultrasound bath at 25° C. It was left to rest for 15 min, repeating the operation twice in total. Later, the mixture was centrifuged. The supernatant was removed, and the residue was extracted a further two times. The corresponding supernatants were combined, and the mixture was dried at low pressure in a rotavap. The residue was redissolved in 40 mL of distilled water, and it was extracted with ethyl acetate. The organic phases were combined. Later, the extract was dried in a rotavap at a temperature lower than 40° C. to obtain a dry extract. The polyphenol content of this extract #1 was 78.3 mg/g, the process yield being 2.1%.

Figure 2A:
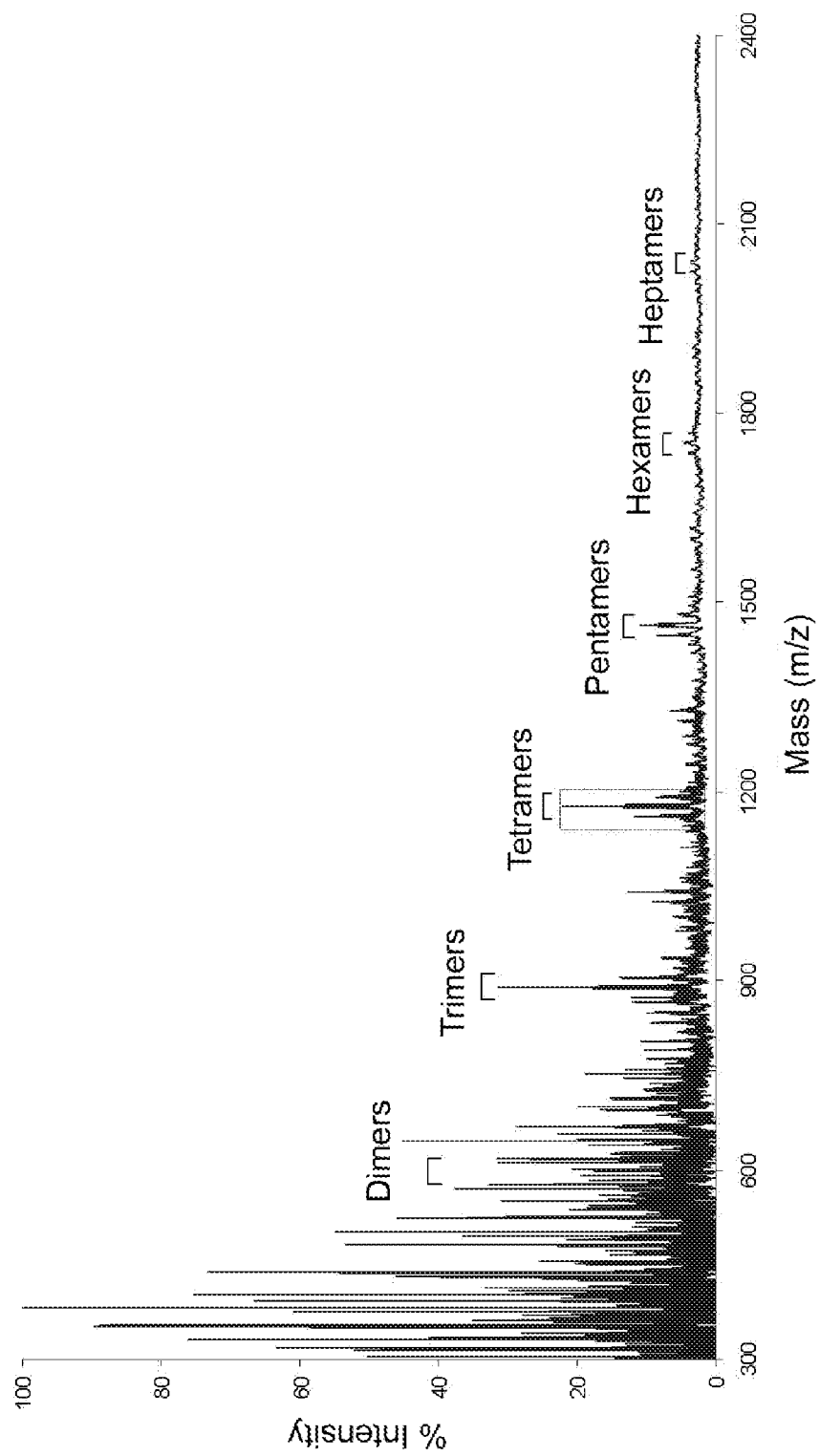
FIGS. 2A and 2B are a MALDI-TOF analysis of the sample obtained in Example 1, enlarging the area corresponding to the tetramers. The presence of procyanidins, propelargonidins, and prodelphinidins from dimers to heptamers, containing both types of bonds, B and A, is verified. Next, the m/z signals corresponding to the sodium adducts [M+Na]$^+$ of the proanthocyanidinins detected are indicated.
Figure 2B:
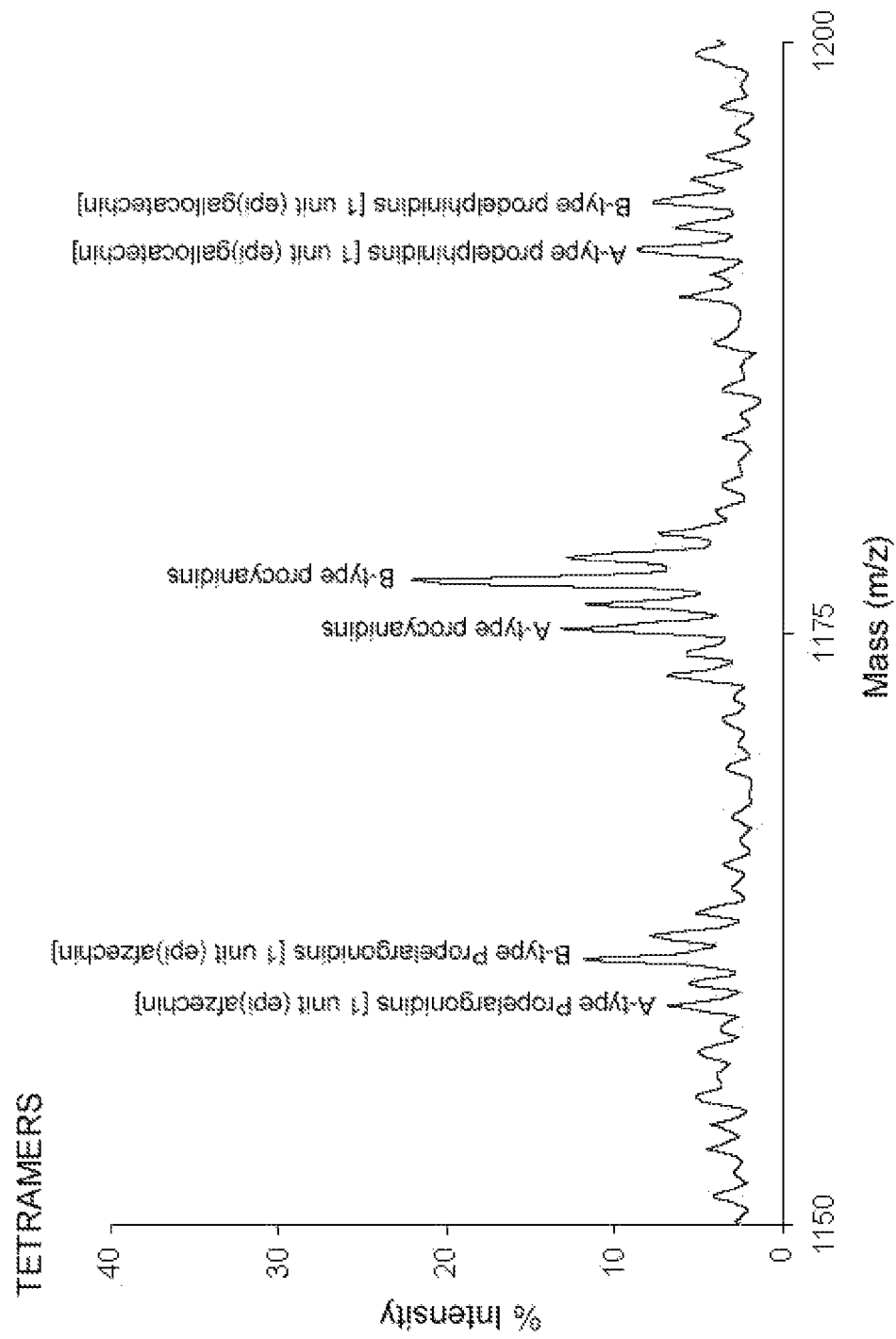

A MALDI-TOF analysis was carried out of the extract using 2.5-dihydroxybenzoic acid (gentisic acid) as matrix. Thus, it was verified that the extract contained procyanidins, propelargonidins, and prodelphinidins up to heptamers (FIG. 2A). Likewise, it was verified that the procyanidins, propelargonidins, and prodelphinidins found corresponded to both types, A and B (FIG. 2B, showing FIG. 2A enlarged for tetramers). Below, the m/z signals are indicated corresponding to the sodium adducts $[M+Na]^+$ of the proanthocyanidinins detected:

Example 1

MALDI-TOF-MS Signals $[M+Na]^+$ (m/z)

| | Procyanidins | | Propelargonidins 1 unit (epi)afzelechin | | Prodelphinidins 1 unit (epi)gallocatechin | |
|---|---|---|---|---|---|---|
| g | B-type | A-type 1 bond | B-type | A-type 1 bond | B-type | A-type 1 bond |
| 2 | 601 | 599 | 585 | 583 | 617 | 615 |
| 3 | 889 | 887 | 873 | | 905 | 903 |
| 4 | 1177 | 1175 | 1161 | 1159 | 1193 | 1191 |
| 5 | 1465 | 1463 | 1449 | | 1481 | 1479 |
| 6 | 1753 | 1751 | 1737 | | | 1767 |
| 7 | 2040* | | 2024* | | | | g-Degree of polymerization.

*Indicates overlapping of the signals corresponding to B and A-type proanthocyanidinins.

An HPLC analysis was also carried out using a Waters Nova-Pak® $C_{18}$ reverse phase column [300 mm×3.9 mm (internal diameter); particle size: 4 µm] and applying an elution gradient composed of water/acetic acid (98:2, v/v) and water/acetonitrile/acetic acid, (73:25:2, v/v/v) with a flow of 1.0 mL/min. A sample volume was injected of 75 µL of a solution of the extract 21 mg/ml in methanol/water (50:50, v/v).

Figure 3:
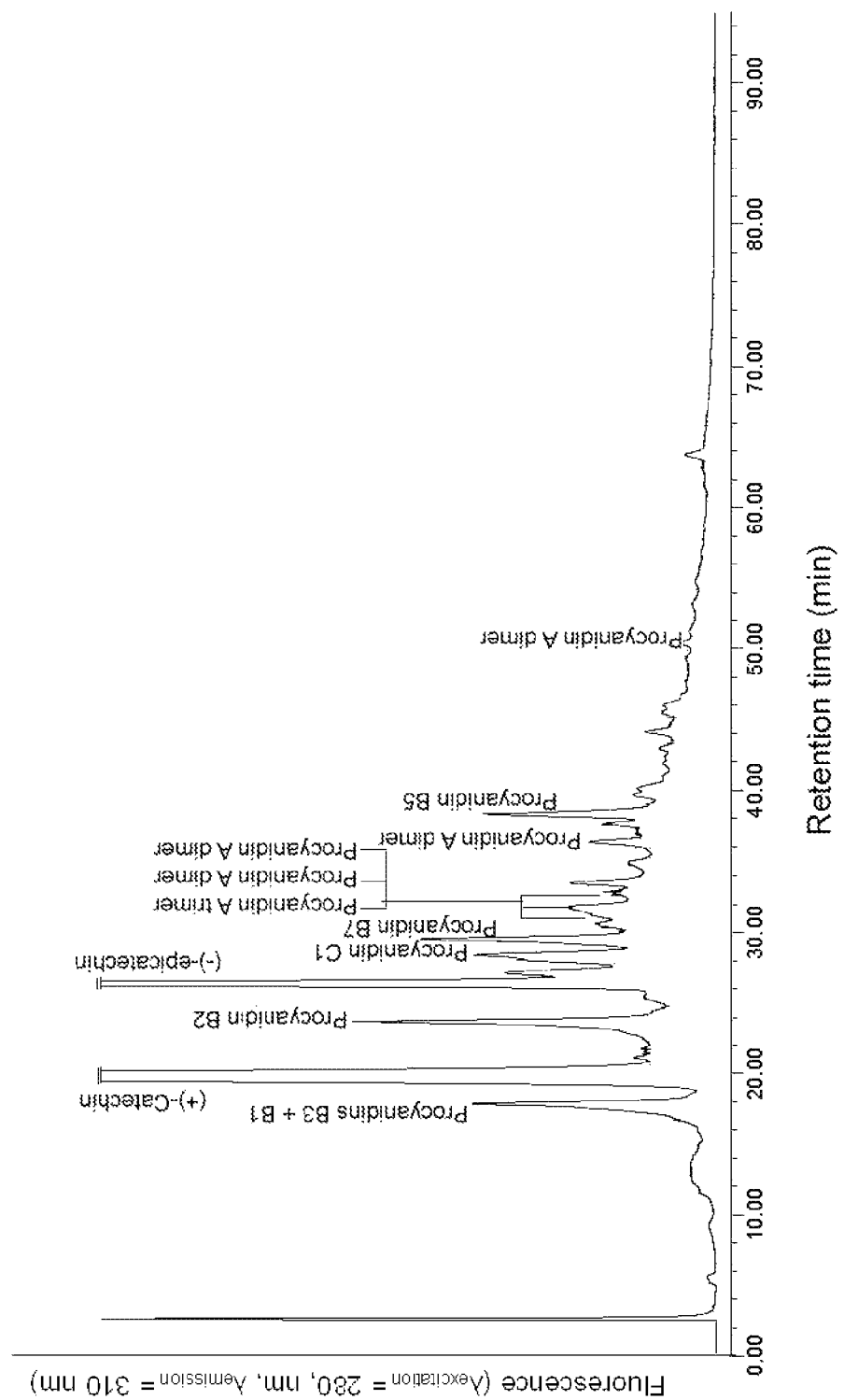
FIG. 3 shows an HPLC analysis with reverse phase column of the sample obtained in Example 1, with identification of chromatographic peaks corresponding to dimers and trimers of B-type procyanidins (m/z=577 and 865, respectively) and dimers and trimers of A-type procyanidins (m/z=575 and 863, respectively).

On the one hand, a quadrupole mass detector was used coupled to an electrospray ionization interface (ESI) which allowed identifying some chromatographic peaks as dimers and trimers of B-type procyanidins (m/z=577 and 865, respectively) and dimers and trimers of A-type procyanidins (m/z=575 and 863, respectively) (FIG. 3). It was not possible to assign chromatographic peaks corresponding to other types of compounds detected by MALDI-TOF analysis (i.e. propelargonidins and prodelphinidins), possibly due to the low concentration thereof and/or coelution between them.

Since there were standards of dimers and trimers of B-type procyanidins previously isolated from other plants, it was possible to assign the chemical structure of the compounds: B3 [(+)-catechin-(4α→8)-(+)-catechin], B1 [(−)-epicatechin-(4β→8)-(+)-catechin], B2 [(−)-epicatechin-(4β→8)-(−)-epicatechin], B7 [(−)-epicatechin-(4β→6)-(+)-catechin], B5 [(−)-epicatechin-(4β→6)-(−)-epicatechin] and C1 [(−)-epicatechin-(4β→8)-(−)-epicatechin-(4β→8)-(−)-epicatechin]. However, it was not possible to assign structures to the rest of the chromatographic peaks due to lack of standards available.

Furthermore, using a fluorescence detector, the chromatographic peak area corresponding to the compounds identified was determined and its content was calculated using the calibrated curve of (−)-epicatechin. Below, the content of the B and A-type proanthocyanidinins identified in almond skin extract is indicated:

Extract #1: Composition

| Phenolic compound | Concentration (mg/g) |
|---|---|
| (+)-Catechin | 6.50 |
| (−)-Epicatechin | 4.48 |
| Procyanidins dimers B (B3 + B1) | 1.41 |
| Procyanidin B dimer (B2) | 1.41 |
| Procyanidin B dimer (B7) | 1.11 |
| Procyanidin B dimer (B5) | 0.70 |
| Procyanidin B trimer (C1) | 1.25 |
| Procyanidin A dimer (tr = 31.8 min) | 0.52 |
| Procyanidin A dimer (tr = 32.9 min) | 0.23 |
| Procyanidin A dimer (tr = 36.4 min) | 0.31 |
| Procyanidin A dimer (tr = 50.6 min) | 0.07 |
| Procyanidin A trimer (tr = 31.4 min) | 0.26 |
| TOTAL | 18.25 |

The total content of flavan-3-ol compounds was 18.25 mg/g, expressed as (−)epicatechin. From these, 7.27 mg/g correspond to proanthocyanidin dimers and trimers. Of this total proanthocyanidinins, 1.39 mg/g correspond to A-type dimers and trimers, in other words 19.0% of proanthocyanidinins identified have an A-type bond.

It also determined the antioxidant capacity of the extract following the ORAC method which evaluates the oxygen radical absorption capacity. This extract #1 has a good antioxidant capacity, its ORAC value being 3.0 mmols of Trolox/g.

Example 2

Extract of Almond Skin Containing Procyanidins, Propelargonidins, and Prodelphinidins The wet almond skin wet shed from the industrial blanching of the fruit was extracted with ethanol acidulated with HCl, pH=3, maintaining a reflux during 4 hours at a temperature close to its boiling point. The skin/acidulated ratio was 1/10. The mixture was pressed and the remains of the skin were separated from the extractive liquid by filtration on 0.2 mm fine mesh. The resulting liquid was dried in a vacuum at a temperature below 60° C.

The dry extract was resuspended in water acidulated with HCl at pH=3, with an extract/water ratio of 1/10. The insoluble dried residue was filtered with fine pore filter paper. The solid residue deposited on the filter was washed with water (pH=3), and the filtered liquid was recovered, being added to the previous liquid.

The extract of almond skin purified and dissolved in water was loaded in a column full of Amberlite XAD-7 resin, previously washed with 5 volumes of ethanol and 5 volumes of distilled water acidulated at pH=3. After the passage of all the extraction liquid, the resin was washed with 2 volumes of 20% ethanol aqueous solution column and, after checking that dry dissolved matter did not come out through the column, the material retained was eluded with 5 volumes of an ethanol/water solution (60/40). This last fraction was dried under vacuum at a temperature lower than 40° C. The total polyphenol content of this extract #2 was 264.6 mg/g, the process yield being 3.3%.

Figure 4A:
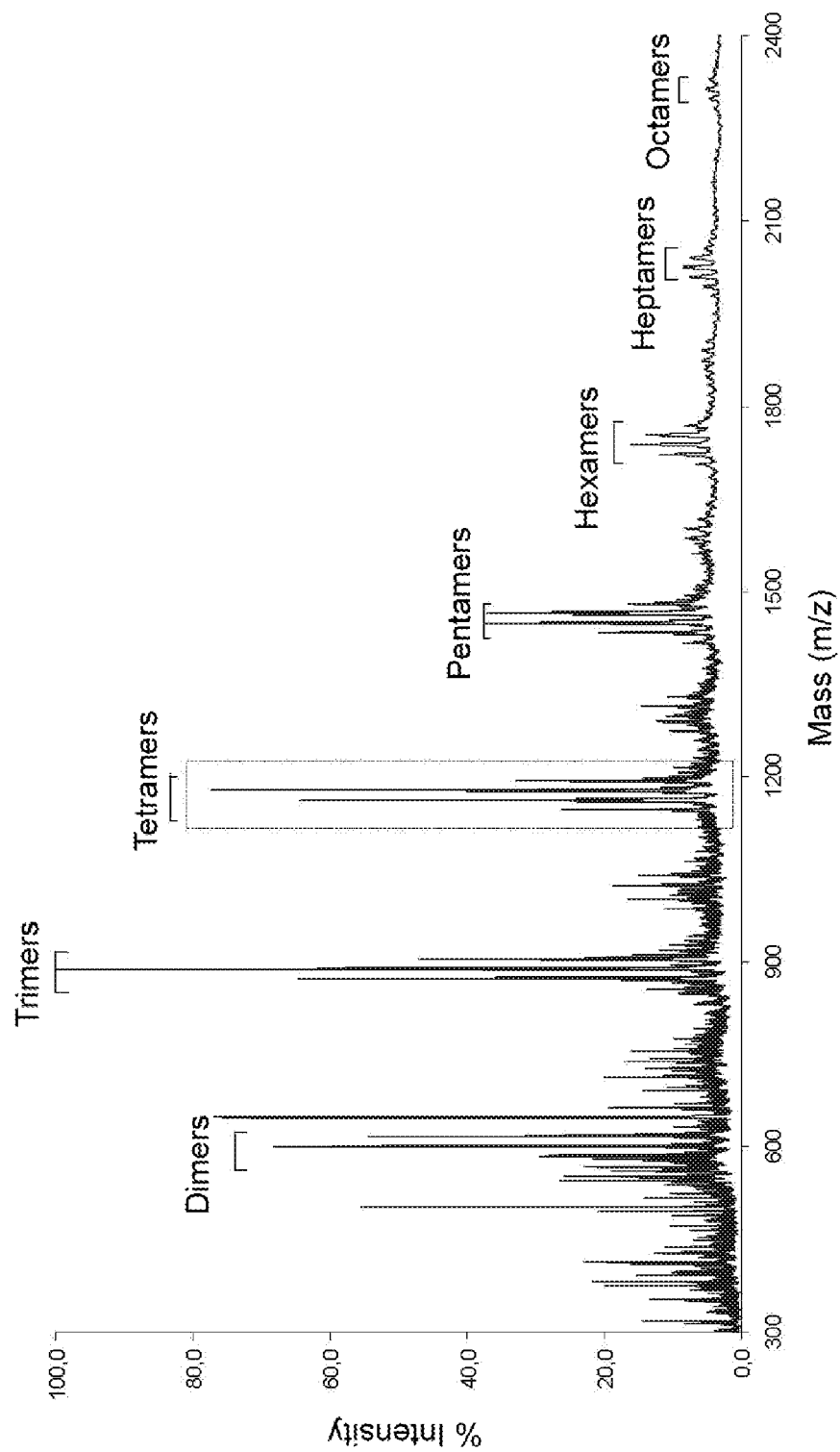
FIGS. 4A and 4B are a MALDI-TOF analysis of the sample obtained in Example 2, enlarging the area corresponding to the tetramers. The presence of procyanidins, propelargonidins, and prodelphinidins from dimers to heptamers, containing both types of bonds, B and A, is verified. Next, the m/z signals corresponding to the sodium adducts [M+Na]$^+$ of the proanthocyanidinins detected are indicated.
Figure 4B:
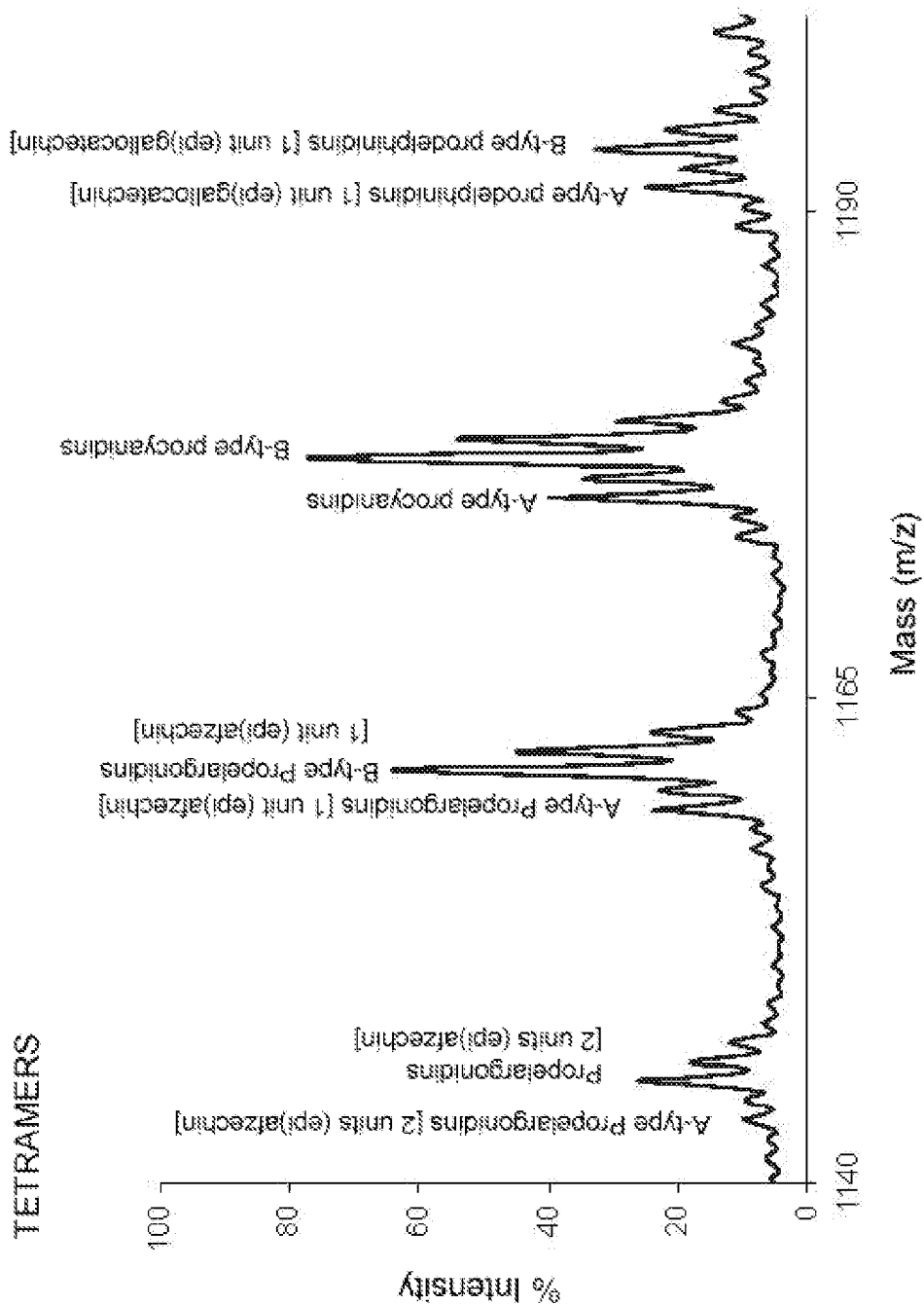

A MALDI-TOF analysis was carried out of the extract using 2.5-dihydroxybenzoic acid (gentisic acid) as matrix. Thus, it was verified that the extract #2 contained procyanidins, propelargonidins, and prodelphinidins up to heptamers (FIG. 4A). Likewise, it was verified that the procyanidins, propelargonidins, and prodelphinidins found corresponded to both types, A and B (FIG. 4B, showing FIG. 4A enlarged for tetramers). Below, the m/z signals are indicated corresponding to the sodium adducts [M+Na]$^+$ of the proanthocyanidinins detected:

MALDI-TOF-MS Signals [M+Na]$^+$ (m/z)

| | Procyanidins | | Propelargonidins 1 (epi)afzelechin unit | | Propelargonidins 2 (epi)afzelechin unit | |
|---|---|---|---|---|---|---|
| g | B-type | A-type 1 bond | B-type | A-type 1 bond | B-type | A-type 1 bond |
| 2 | 601 | 599 | 585 | 583 | | 567 |
| 3 | 889 | 887 | 873 | 871 | 857 | |
| 4 | 1177 | 1175 | 1161 | 1159 | 1145 | 1143 |
| 5 | 1465 | 1463 | 1449 | 1447 | 1433 | 1431 |
| 6 | 1753 | 1751 | 1737 | 1735 | 1721 | 1719 |
| 7 | 2040* | | 2024* | | 2008* | |
| 8 | 2028* | | 2312* | | 2296* | |

MALDI-TOF-MS Signals [M+Na]$^+$ (m/z)

| | Prodelphinidins 1 (epi)gallocatechin unit | | Prodelphinidins 2 (epi)gallocatechin units | |
|---|---|---|---|---|
| g | Type B | A-type 1 bond | B-type | A-type 1 bond |
| 2 | 617 | 615 | 633 | 631 |
| 3 | 905 | 903 | | 919 |
| 4 | 1193 | 1191 | | |
| 5 | 1481 | 1479 | | |
| 6 | 1769 | 1767 | | |
| 7 | | 2056* | | | g-Degree or polymerization.
*Indicates overlapping of the signals corresponding to B and A-type proanthocyanidinins.

An HPLC analysis was also carried out using a Waters Nova-Pak® $C_{18}$ reverse phase column [300 mm×3.9 mm (internal diameter); particle size: 4 μm] and applying an elution gradient composed of water/acetic acid (98:2, v/v) and water/acetonitrile/acetic acid, (73:25:2, v/v/v) with a flow of 1.0 mL/min. A sample volume was injected of 5 μL of a solution of the extract of 43 mg/ml in methanol/water (50:50, v/v).

Figure 5:
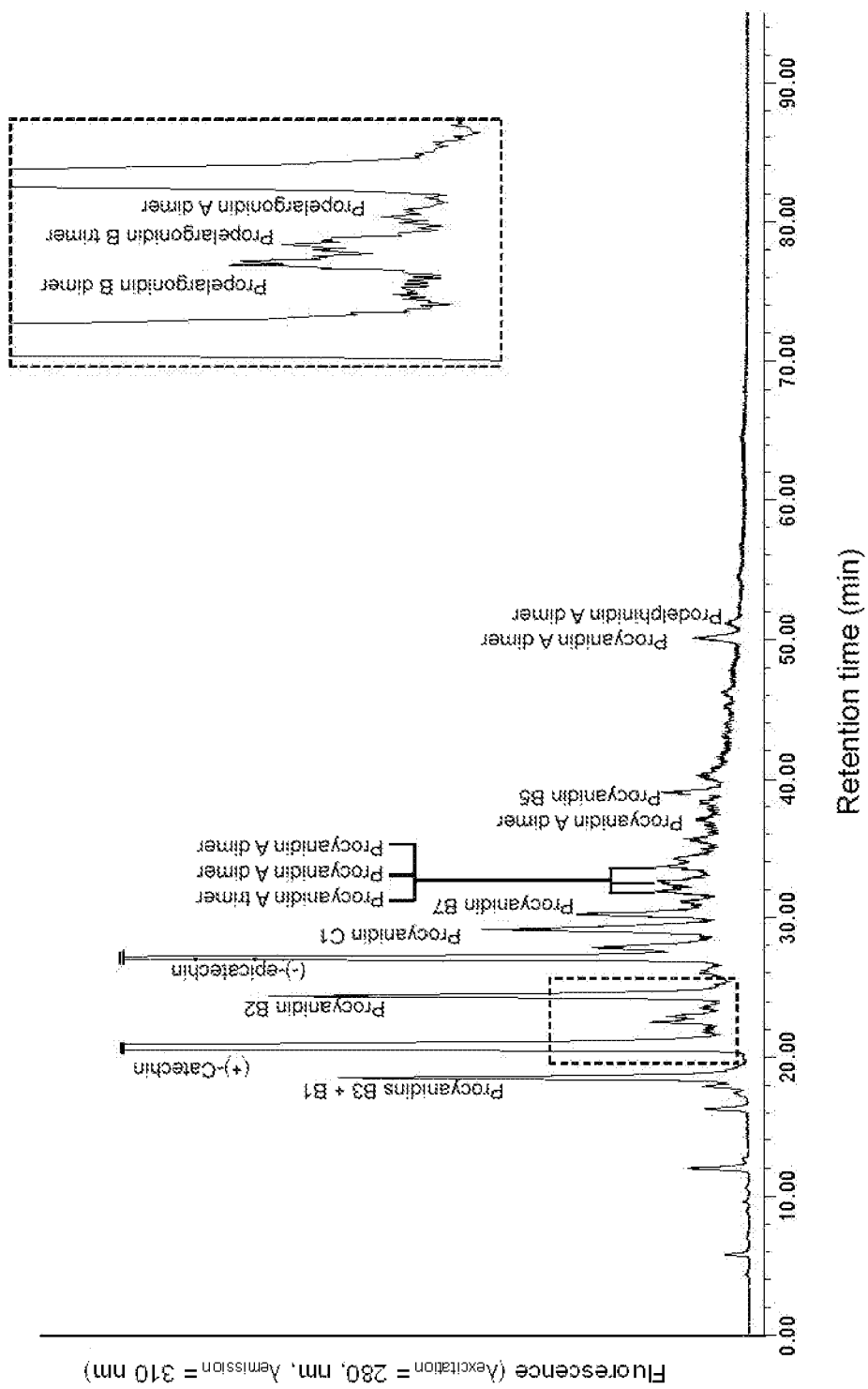
FIG. 5 shows an HPLC analysis with reverse phase column of the sample obtained in Example 2, with identification of chromatographic peaks corresponding to dimers and trimers of B-type procyanidins (m/z=577 and 865, respectively), dimers and trimers of A-type procyanidins (m/z=575 and 863, respectively), dimers and trimers of B-type propelargonidins (m/z=561 and 849, respectively), dimers of A-type propelargonidins (m/z=559), and dimers of A-type prodelphinidins (m/z=591).

On the one hand, a quadrupole mass detector was used coupled to an electrospray ionization interface (ESI) which allowed identifying some chromatographic peaks as dimers and trimers of B-type procyanidins (m/z=577 and 865, respectively), dimers and trimers of A-type procyadinins (m/z=575 and 863, respectively), dimers and trimers of B-type propelargonidins (m/z=561 and 849, respectively), dimers of A-type propelargonidins (m/z=559) and dimers of A-type prodelphinidins (m/z=591) (FIG. 5). It was not possible to assign chromatographic peaks corresponding to other types of compounds detected by MALDI-TOF analysis (i.e. propelargonidins, and prodelphinidins) possibly due to the low concentration thereof and/or coelution between them.

Since there were standards of dimers and trimers of B-type procyanidins previously isolated from other plants, it was possible to assign the chemical structure of the compounds:

B3 [(+)-catechin-(4α→8)-(+)-catechin], B1 [(−)-epicatechin-(4β→8)-(+)-catechin], B2 [(−)-epicatechin-(β→8)-(−)-epicatechin], B7 [(−)-epicatechin-(4β→6)-(+)-catechin], B5 [(−)-epicatechin-(4β→6)-(−)-epicatechin] and C1 [(−)-epicatechin-(4β→8)-(−)-epicatechin-(4β→8)-(−)-epicatechin]. However, it was not possible to assign structures to the rest of the chromatographic peaks due to lack of standards available.

Furthermore, using a fluorescence detector, the chromatographic peak area corresponding to the compounds identified was determined and its content was calculated using the calibrated curve of (−)-epicatechin. Below, the content of the B and A-type proanthocyanidinins identified in almond skin extract is indicated:

Extract #2: Composition

| Phenolic compound | Concentration (mg/g) |
| --- | --- |
| (+)-Catechin | 40.82 |
| (−)-Epicatechin | 19.81 |
| Procyanidin B dimers (B3 + B1) | 10.75 |
| Procyanidin B dimer (B2) | 11.42 |
| Procyanidin B dimer (B7) | 5.22 |
| Procyanidin B dimer (B5) | 2.22 |
| Procyanidin B trimer (C1) | 8.02 |
| Procyanidin A dimer (tr = 32.7 min) | 2.95 |
| Procyanidin A dimer (tr = 33.7 min) | 2.48 |
| Procyanidin A dimer (tr = 36.9 min) | 1.74 |
| Procyanidin A dimer (tr = 50.1 min) | 1.47 |
| Procyanidin A trimer (tr = 32.0 min) | 2.13 |
| Propelargonidin B dimer (tr = 22.5 min) | 1.90 |
| Propelargonidin B trimer (tr = 22.9 min) | 1.66 |
| Propelargonidin A dimer (tr = 23.6 min) | 0.80 |
| Prodelphinidin A dimer (tr = 51.1 min) | 0.63 |
| TOTAL | 114.02 |

The total content of flavan-3-ol compounds was 114.02 mg/g, expressed as (−)epicatechin. From these, 53.39 mg/g correspond to proanthocyanidin dimers and trimers. Of this total proanthocyanidinins, 12.2 mg/g correspond to A-type dimers and trimers, in other words, 21.4% of proanthocyanidinins identified have an A-type bond.

It also determined the antioxidant capacity of the extract following the ORAC method which evaluates the oxygen radical absorption capacity. This extract #2 has a good antioxidant capacity, its ORAC value being 12.1 mmols of Trolox/g.

Example 3

Extract of Almond Skin Containing Procyanidins, Propelargonidins, and Prodelphinidins The same sample of almond skin was used as in Example 2. The same extracting liquid was also used (ethanol acidulated with HCl (pH=3)), but a specific extractor apparatus was used that made it possible to use liquids at high temperatures and pressures. The working conditions were 2000 psi pressure and 90° C. temperature, the extraction time being 30 min. The resulting liquid was subjected to vacuum drying at a temperature below 60° C. From this point, the same steps were done as in Example 2, and the analysis for characterization of the extract and identification of its components were carried out in the same way, obtaining an extract substantially equivalent to that obtained in Example 2.

Having sufficiently described the nature of the various example embodiments, it should be stated that the aforementioned embodiments may have their details modified provided it does not alter the fundamental principle.

The invention is, of course, not limited to the examples described but cover all the variants defined in the claims. The terms "a" and "an" and "the" and similar references used in the context of the following claims are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g. "such as") provided herein is intended merely to better illuminate the embodiments and does not pose a limitation on the scope of the embodiments otherwise claimed. No language in the specification should be construed as indicating any non-claimed element essential to the practice of the embodiments.

The use of the term "or" in the claims is used to mean "and/or" unless explicitly indicated to refer to alternatives only or the alternatives are mutually exclusive, although the disclosure supports a definition that refers to only alternatives and "and/or." Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments are described herein, including the best mode known to the inventors for carrying out the invention. Of course, variations on those preferred embodiments will become apparent to those of ordinary skill in the art upon reading the foregoing description. The inventors expect those of ordinary skill in the art to employ such variations as appropriate, and the inventors intend for the embodiments to be practiced otherwise than specifically described herein. Accordingly, these embodiments include all modifications and equivalents of the subject matter recited in the claims appended hereto as permitted by applicable law. Moreover, any combination of the above-described elements in all possible variations thereof are encompassed by the embodiments unless otherwise indicated herein or otherwise clearly contradicted by context.

Further, it is to be understood that the example embodiments disclosed herein are illustrative. Other modifications that may be employed are within the scope of the embodiments. Thus, by way of example, but not of limitation, alternative configurations of the present embodiments may be utilized in accordance with the teachings herein. Accordingly, the present embodiments are not limited to that precisely as shown and described.

The invention claimed is:

1. An extract of almond skin, wherein said extract of almond skin has a phenolic content greater than about 50 mg/g, and wherein said extract of almond skin comprises dimers and trimers of A-type proanthocyanidinins in a percentage of at least about 1.77% by weight of the total phenolic content, wherein the dimers and trimers of A-type proanthocyanidinins include procyanidins, propelargonidins and prodelphinidins.

2. The extract of almond skin of claim 1, wherein the percentage of dimers and trimers of A-type proanthocyanidinins is between about 1.77% and 4.61% by weight of the total phenolic content.

3. The extract of almond skin according to claim 1, obtained by a process comprising:
   a) obtaining the almond skin from an almond fruit, said obtaining comprising at least one of blanching, peeling, toasting, grinding, and combinations thereof;
   b) extracting the obtained skin with an organic solvent-selected from methanol or ethanol, pure or mixed with water, further comprising an organic or inorganic acid, wherein said extracting step is carried out by at least one of the following:
      (i) ultrasound bath,
      (ii) overheating the organic solvent at a temperature between about 60° C. and about 180° C. and at a pressure between about 500 psi and about 3000 psi, or
      (iii) reflux; and
   c) purifying the extract, said purifying comprising at least one of extracting with a solvent, adsorption, and ion exchange chromatography.

4. The extract of almond skin of claim 3, wherein the process further comprises drying the purified extract.

5. The extract of almond skin of claim 3, wherein said obtaining step further comprises defatting the skin with an organic solvent.

6. The extract of almond skin of claim 5, wherein the organic solvent is hexane.

7. The extract of almond skin of claim 3, wherein the purification step is carried out by extraction with at least one of ethyl acetate, acetone, n-butanol, iso-propanol, and mixtures thereof.

8. The extract of almond skin of claim 3, wherein the purification step is carried out by adsorption or ion exchange chromatography on a resin by elution in alcohol gradient of 20% and 80%.

9. A pharmaceutical composition comprising the extract of almond skin of claim 1 and a carrier.

10. The extract of almond skin of claim 3, wherein the acid is selected from the group consisting of HCl, $H_2SO_4$, $H_3PO_4$, acetic acid, citric acid, or a cationic resin in protonated form.

11. The extract of almond skin of claim 4, wherein the drying is carried out at a temperature below about 40° C.

12. The extract of almond skin of claim 4, wherein the drying comprises at least one of lyophilisation, concentration, vacuum drying, air drying, and spraying.

13. The extract of almond skin of claim 3, wherein the extraction step (b) is carried out in an ultrasound bath at a temperature between about 25° C. and about 100° C., for a time between about 2 hours and about 24 hours.

14. The extract of almond skin of claim 13, wherein the organic solvent of extraction step (b) is methanol/HCl in a proportion of 1000:1 by volume; wherein the extract is purified by extraction with ethyl acetate; and wherein the purified extract is concentrated to dry at a drying temperature below about 40° C.

15. The extract of almond skin of claim 3, wherein the organic solvent of extraction step (b) is ethanol/HCl at pH=3; wherein the extract is purified by column chromatography; and wherein the purified extract is vacuum dried at a drying temperature below about 60° C.

16. The extract of almond skin of claim 3, wherein the extraction time is about 4 hours.

17. The extract of almond skin of claim 3, wherein the extraction step (b) is carried out with the organic solvent overheated between about 100° C. and about 140° C., and wherein the extraction time is between about 1 minute and about 6 hours.

18. A functional food or dietary supplement comprising the extract of almond skin according to claim 1.

19. The extract of claim 1 wherein the procyanidins comprise catechin units.

20. The extract of claim 1 wherein the propelargonidins comprise afzelechin units.

21. The extract of claim 1 wherein the prodelphinidins comprise gallocatechin units.

22. The extract of claim 1 wherein the procyanidins comprise epicatechin units.

23. The extract of claim 1 wherein the propelargonidins comprise epiafzelechin units.

24. The extract of claim 1 wherein the prodelphinidins comprise epigallocatechin units.

* * * * *